(12) United States Patent
Kabata

(10) Patent No.: US 8,765,397 B2
(45) Date of Patent: Jul. 1, 2014

(54) CELL DISPERSION METHOD, CELL DISPERSING AGENT AND CELL MEASUREMENT METHOD

(75) Inventor: Hiroyuki Kabata, Kyoto (JP)

(73) Assignee: Sysmex Corporation, Hyogo (JP)

( * ) Notice: Subject to any disclaimer, the term of this patent is extended or adjusted under 35 U.S.C. 154(b) by 548 days.

(21) Appl. No.: 13/003,273

(22) PCT Filed: Jul. 10, 2009

(86) PCT No.: PCT/JP2009/062598
§ 371 (c)(1),
(2), (4) Date: Jan. 7, 2011

(87) PCT Pub. No.: WO2010/005078
PCT Pub. Date: Jan. 14, 2010

(65) Prior Publication Data
US 2011/0117593 A1 May 19, 2011

(30) Foreign Application Priority Data
Jul. 10, 2008 (JP) .................................. 2008-180438

(51) Int. Cl.
*C12Q 1/02* (2006.01)

(52) U.S. Cl.
USPC .............................. 435/29; 526/249; 526/250

(58) Field of Classification Search
USPC ............................................................ 435/29
See application file for complete search history.

(56) References Cited

U.S. PATENT DOCUMENTS

| 6,599,718 B1 | 7/2003 | Liu |
| 2005/0058632 A1 | 3/2005 | Hedrick |

FOREIGN PATENT DOCUMENTS

| EP | 0483760 A2 | 5/1992 |
| EP | 1 688 503 A1 | 8/2006 |
| WO | 2005/038044 A1 | 4/2005 |
| WO | WO 2007/148341 A2 | 12/2007 |

OTHER PUBLICATIONS

The Japanese Tissue Culture Association, "Soshiki Baiyo no Gijutsu", Asakura Shoten, Aug. 1983, p. 23.
Shinbagaki N., et al., "Functional Analysis of CD82 in the Early Phase of T Cell Activation: Roles in Cell Adhesion and Signal Transduction", Eur. J. Immunol, 1998, pp. 1125-1133, vol. 28.
Murata Y., et al., "Differential Localization of the Vacuolar $H^+$Pump with G Subunit Isoforms (G1 and G2) in Mouse Neurons", J. Biol. Chem., 2002, pp. 36296-36303, vol. 277.
S.A. Engelholm et al: "Disaggregation of human solid tumours by combined mechanical and enzymatic methods", British Journal of Cancer, vol. 51, No. 1, Jan. 1, 1985, pp. 93-98, XP55005214.
Cunningham R. E.: "Tissue disagrreagation,", Methods in Molecular Biology (Clifton, N. J.) 1999 Lnke-Pubmed: 10098188, vol. 155, 1999, pp. 257-260, XP008141500.
Klimetzek V, et al; "The murine bone marrow macrophage, a sensitive indicator cell for murine migration inhibitory factor and a new method for their harvest"; Celluar Immunilogy Academic Press, San Diego, CA, US, vol. 53, No. 2, Aug. 1, 1980, pp. 257-266, XP024006156.
Freshney, R. I.: "Principles of Tissue Culture and Bioreactro Design/Chapter 12 IN: 'Principles of Tissue Engineering", 2007, Elsevier, XP008141511, vol. Third, pp. 155-182.

*Primary Examiner* — Taeyoon Kim
*Assistant Examiner* — Tiffany Gough
(74) *Attorney, Agent, or Firm* — Sughrue Mion, PLLC

(57) ABSTRACT

A cell dispersion method, a cell dispersing agent and a cell measurement method, each of which can disperse a cell mass while reducing damage to a cell are provided. Upon dispersing a cell mass, a fluororesin particle is used. A cell mass composed of an aggregated of multiple cells is mixed with a fluororesin particle in a liquid medium, thereby separating the cell mass into individual cells to disperse the cells. In addition, the dispersed cells are measured by flow cytometry, thereby carrying out cell measurement.

13 Claims, 14 Drawing Sheets

CELL DISPERSION METHOD, CELL DISPERSING AGENT AND CELL MEASUREMENT METHOD

TECHNICAL FIELD

The present invention relates to a cell dispersion method, a cell dispersing agent and a cell measurement method. More specifically, the present invention relates to a cell dispersion method, a cell dispersing agent and a cell measurement method, in which a cell mass formed during cell culture or a cell mass collected from a living body is dispersed.

BACKGROUND ART

Cells collected from a cell culture or a uterine cervix aggregate to form a cell mass composed of multiple cells. Therefore, when the cells are used for microscopic observation (for example, cytological diagnosis) or measured using a flow cytometer, it is necessary to carry out a dispersion treatment of the cell mass as a pretreatment.

For example, Patent Literature 1 discloses a method using a proteolytic enzyme such as trypsin as a method for dispersing a cell mass. However, for example, when a cell mass contained in a medium is dispersed using a proteolytic enzyme, a protein contained in the medium is preferentially degraded. Consequently, the cell dispersion effect is insufficient. In addition, when a cell mass stored in an alcohol solution (fixed) is dispersed using a proteolytic enzyme, the cell dispersion effect is also insufficient.

On the other hand, when a cell mass contained in a phosphate buffered saline (PBS) is dispersed using a proteolytic enzyme, the proteolytic enzyme can disperse the cell mass. However, in a prolonged reaction, the proteolytic enzyme sometimes lyses a cell membrane. In addition, when a cell mass containing a mucus-attached cell such as a cervical cell is dispersed, a proteolytic enzyme preferentially degrades the mucus. Consequently, the cell dispersion effect is insufficient.

There is thus a possibility that a cell which is not dispersed sufficiently or a damaged cell affects microscopic observation (for example, cytological diagnosis) or measurement by flow cytometry.

CITATION LIST

Patent Literature

Patent Literature 1: International Publication 2005/038044 pamphlet

SUMMARY OF INVENTION

The present invention was made in the light of the circumstances as described above, and it is an object of the present invention to provide a cell dispersion method, a cell dispersing agent, each of which can disperse a cell mass while reducing damage to a cell, and a cell measurement method using the method and the agent.

The present invention provides a cell dispersion method, comprising the step of separating a cell mass composed of an aggregate of multiple cells into individual cells to disperse the cells in a liquid medium, wherein the cell mass is mixed with a fluororesin particle in a liquid medium. In addition, the present invention provides a cell dispersing agent for dispersing a cell mass, comprising a fluororesin particle. Furthermore, the present invention provides a cell measurement method containing the steps of: a mixing step in which a cell mass composed of an aggregate of multiple cells is mixed with a fluororesin particle in a liquid medium, and a step of measuring the mixture obtained in the mixing step with a flow cytometer.

According to the cell dispersion method, the cell dispersing agent and the cell measurement method of the present invention, a cell mass can be dispersed while reducing damage to a cell. Therefore, according to the cell dispersion method, the cell dispersing agent and the cell measurement method of the present invention, a sample to be tested suitable for microscopic observation (for example, cytological diagnosis) or flow cytometry can be prepared. In addition, by such a cell measurement method, cell measurement can be successfully carried out by flow cytometry.

1. CELL DISPERSION METHOD

Figure 1:
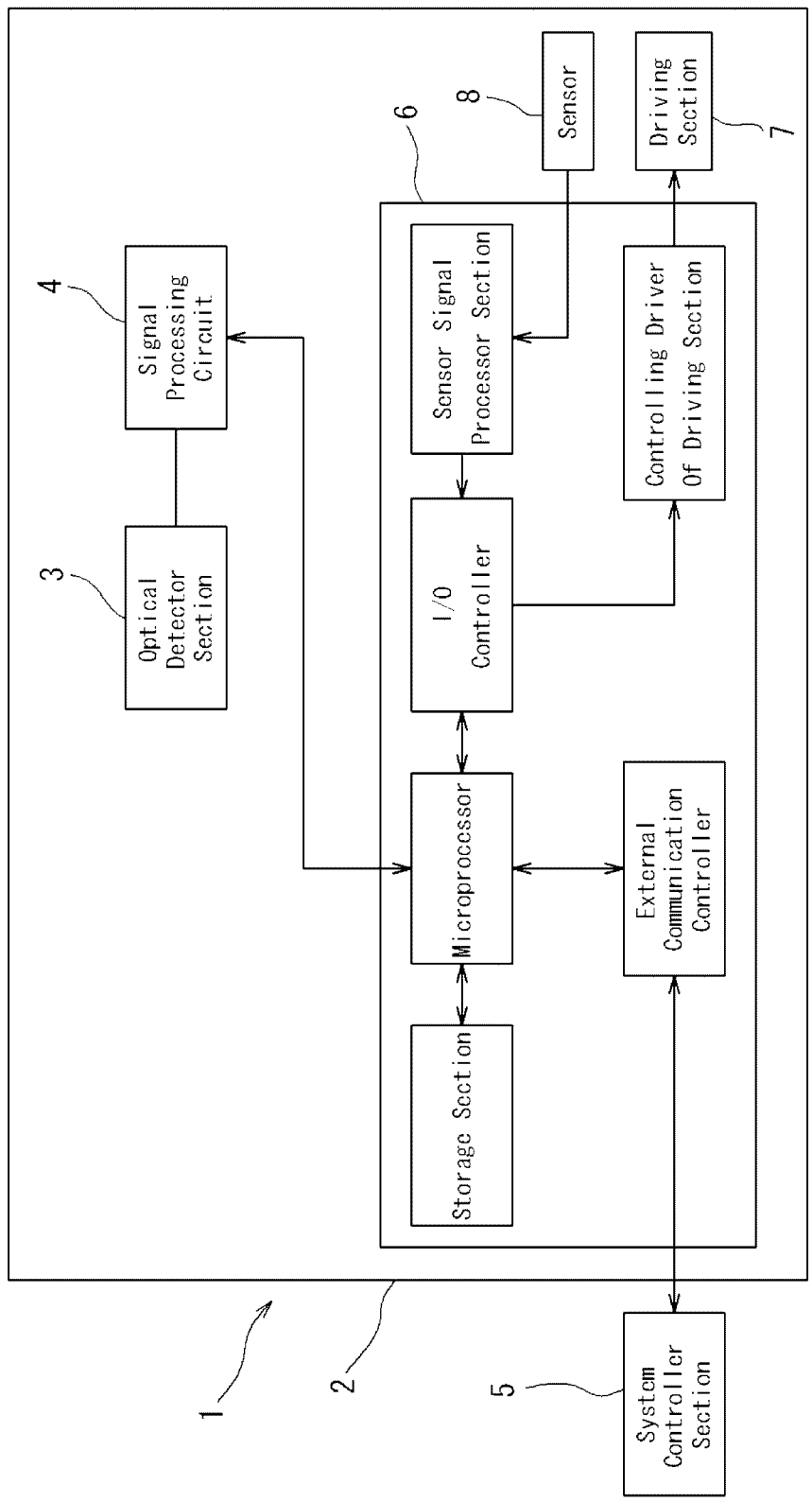
[FIG. 1] A block diagram showing the constitution of a cell analyzer using a flow cytometry technique.

The cell dispersion method of the present invention is a method comprising the step of separating a cell mass composed of an aggregate of multiple cells into individual cells to disperse the cells in a liquid medium, wherein the cell mass is mixed with a fluororesin particle in a liquid medium.

The "cell mass" in the present specification is an aggregate of multiple cells. In the present invention, for example, those containing cells aggregated by mucus, the cells being collected by scraping mucus of a living body can be used as a cell mass. Specific cell masses include, for example, a cell mass containing a cell collected by scraping a uterine cervix, a nasal cavity or a pharynx, and the like. In addition, in the present invention, multiple cells which are stored in an alcohol solution and aggregate can be used as a cell mass. Furthermore, a cell culture obtained by culturing cells collected from a living body can also be used as a cell mass.

In the present specification, to "disperse a cell mass" means to separate cells which constitute a cell mass from the cell mass, thereby breaking up such cells, for example, into a solution. The cell mass to be dispersed in the present invention is a huge structure composed of an aggregate of a single entity and another single entity, an aggregated entity and another aggregated entity or a single entity and an aggregated entity. There is a possibility that the cell mass affects cytological diagnosis or measurement by flow cytometry. On the other hand, the state of the "dispersed cells", which is a target of the dispersion of the present invention, is preferably a state of an aggregated entity wherein two to six cells aggregate or a state of a single entity, and more preferably a state of a single entity.

In the cell dispersion method of the present invention, dispersion of a cell mass is carried out by lubricating the interface between cells (results in shear stress between the cells) by a fluororesin particle entering into a gap among adhered cells, in other words, a gap among the cells. The degree of lubrication in the interface between cells increases in proportion to the rate of fluororesin particles entering into a gap among cells. In other words, it is preferable to increase the rate of fluororesin particles entering into a gap among cells. Therefore, it is preferable that the particle diameter of a fluororesin particle is small. In addition, upon mixing a cell mass with a fluororesin particle, the rate of fluororesin particles entering into a gap among cells increases by increasing the concentration of a fluororesin particle in the mixture containing a cell mass and a fluororesin particle and/or enhancing diffusion of a fluororesin particle. Therefore, in the cell dispersion method of the present invention, a cell mass can be dispersed more efficiently by employing such conditions. In the cell dispersion method of the present invention, since two shear stresses, an internal shear stress associated with an interfacial chemical activity inherent to a fluororesin particle and an external shear stress by hydrodynamic process act on a gap among cells as a synergistic effect with using a fluororesin particle, by further carrying out a step of stirring a mixture containing a cell mass and a fluororesin particle (stirring step) to enhance diffusion of a fluororesin particle in the mixture, the cell mass can be quickly and easily dispersed.

In the present specification, an aqueous solution, a water-soluble organic solvent, and a mixed solvent of an aqueous solution and a water-soluble organic solvent can be used as a liquid medium for dispersing cells. Preferably, the liquid medium is an aqueous solution, or a mixed solvent of an aqueous solution and a water-soluble organic solvent.

The fluororesin which constitutes the fluororesin particle includes, for example, polytetrafluoroethylene (PTFE), tetrafluoroethylene-perfluoroalkyl vinyl ether copolymer (PFA), tetrafluoroethylene-hexafluoropropylene copolymer (FEP), ethylene-tetrafluoroethylene copolymer (ETFE), polyvinylidene fluoride (PVDF), polychlorotrifluoroethylene (PCTFE), ethylene-chlorotrifluoroethylene copolymer (ECTFE), and the like.

In the cell dispersion method of the present invention, the concentration of a fluororesin particle in the mixture is preferably 0.003% by mass or more and 60% by mass or less, and more preferably 0.2% by mass or more and 3% by mass or less.

When the concentration of a fluororesin particle is 0.003% by mass or more, even cells fixe in a cell preservation liquid containing an alcohol can be sufficiently dispersed. In addition, when an unwashed cell mass in a medium is dispersed, the concentration of a fluororesin particle is preferably 0.2% by mass or more. Furthermore, when the concentration of a fluororesin particle is 60% by mass or less, a cell dispersed by the cell dispersion method of the present invention can be favorably used in flow cytometry or microscopic observation. When a test sample (sample to be measured) containing a cell dispersed by the cell dispersion method of the present invention is used in flow cytometry, in order to decrease the influence on measurement of a cell and to more facilitate washing of a flow path, it is preferable that the concentration of a fluororesin particle in the test sample is low. When a test sample containing a cell dispersed by the cell dispersion method of the present invention is used for microscopic observation, in order to carry out the observation without suspending the cell to be observed, it is preferable that the concentration of a fluororesin particle in the test sample is low. Consequently, from the viewpoint of sufficiently dispersing cells and obtaining cells suitable for use in flow cytometry or microscopic observation, the concentration of a fluororesin particle is preferably 3% by mass or less.

The particle diameter of a fluororesin particle can be appropriately selected depending on the size of the cell to be dispersed or on the use of the cell dispersed by the cell dispersion method of the present invention. In order to disperse a cell mass, it is necessary that a fluororesin particle enters into a gap among cells to lubricate the interface between the cells. Consequently, it is preferable that the particle diameter of a fluororesin particle is smaller than that of a cell. The particle diameter of a fluororesin particle is preferably 1/10 or less, and more preferably 1/100 or less, relative to the size of a cell.

Generally, the size of a plant cell is about 200 μm, and the size of an animal cell is about 30 μm. Among animal cells, the size of a cervical cell is sometimes about 60 μm. For example, when a cell mass containing a plant cell of which size is about 200 μm is dispersed, the particle diameter of a fluororesin particle is preferably 200 μm or less, more preferably 20 μm or less, and still more preferably 2 μm or less. When a cell mass containing a cervical cell of which size is about 60 μm is dispersed, the particle diameter of a fluororesin particle is preferably 60 μm or less, more preferably 6 μm or less, and still more preferably 0.6 μm or less. On the other hand, from the viewpoint of inhibiting scattering and the like of the fluororesin particle and facilitating handling of the fluororesin particle, the particle diameter of a fluororesin particle is preferably 0.1 μm or more. In the cell dispersion method of the present invention, it is preferable that a particle mixture containing a particle of which particle diameter is 0.1 μm or more and 200 μm or less is used as the fluororesin particle.

When a test sample containing a cell dispersed by the cell dispersion method of the present invention is used for cytological diagnosis by microscopic observation, if the cell to be observed has about the same size as that of a fluororesin particle, there is a possibility that the microscopic observation is inhibited by the fluororesin particle. Therefore, it is desirable that the particle diameter of a fluororesin particle is 1/10 or less, and more preferably 1/100 or less relative to the size of a cell.

When a test sample containing a cell dispersed by the cell dispersion method of the present invention is used for flow cytometry, the influence of the particle diameter of the fluororesin particle in the test sample on measurement is little. Flow cytometry generally measures the intensity of scattered light reflecting the size of a measured substance and fluorescence intensity reflecting the internal information of the measured substance. While a cell is stained by a visualizing agent to emit fluorescence, a fluororesin particle is not stained by a visualizing agent and does not emit autofluorescence. Consequently, it can be judged by presence of fluorescence whether a measured substance is a cell or a fluororesin particle. When a test sample containing cells dispersed by the cell dispersion method of the present invention is used for flow cytometry, the particle diameter of a fluororesin particle is preferably 1/10 or less, and more preferably 1/100 or less, relative to the size of a cell to be measured. By using a fluororesin particle having such a particle diameter, it can be judged by information on the size obtained by the intensity of scattered light whether the measured substance is a cell or a fluororesin particle. Consequently, an apparatus or a program for measuring fluorescence intensity can be omitted. In addition, in flow cytometry, since the larger the number of the particles to be measured is, the more likely the number of particles measured in the apparatus exceeds the limit value or the more likely the analysis requires a long time, it is more preferable that the number of particles to be measured is small. Consequently, when the particle diameter of a fluororesin particle is sufficiently small relative to the size of a cell, since the measurement of the number of the cells is not inhibited, useless count can be decreased.

The average particle diameter of such a fluororesin particle is preferably 0.1 μm or more, and more preferably 0.2 μm or more, from the viewpoint of ease in handling, and preferably 200 μm or less, more preferably 10 μm or less, and still more preferably 5 μm or less, from the viewpoint of lubrication of the interface between cells. Here, the average particle diameter means number average diameter determined by a light scattering method.

In the cell dispersion method of the present invention, the cell mass may be a cell mass adhered to a cell culture substrate. As a conventional method for dispersing a cell mass adhered to a cell culture substrate, a cell dispersion method using a proteolytic enzyme is known. However, in this method, when a proteolytic enzyme is reacted with a cell mass for a long time, the proteolytic enzyme sometimes lyses the cell membrane of a cell which constitutes the cell mass. In contrast, since the fluororesin particle is used in the cell dispersion method of the present invention, the cell dispersion method of the present invention is advantageous in that a cell mass is stripped off from the cell culture substrate, thereby enabling dispersion into individual cells, without damaging a cell which constitutes the cell mass.

In addition, in the cell dispersion method of the present invention, a cell mass before mixed with a fluororesin particle maybe contained in a medium. In the present invention, a medium maybe any of a solid medium, a semisolid medium and a liquid medium. The cell mass may be either a cell mass adhered to a cell culture substrate or a cell mass not adhered to a cell culture substrate. By the way, when a cell mass contained in a medium is conventionally dispersed using a proteolytic enzyme, the proteolytic enzyme preferentially degrades a protein contained in the medium. Consequently, the cell dispersion effect is insufficient. In contrast, since the fluororesin particle is used in the cell dispersion method of the present invention, the cell dispersion method of the present invention is advantageous in that a cell mass in a medium can be sufficiently dispersed.

Furthermore, in the cell dispersion method of the present invention, a cell mass before mixed with a fluororesin particle may be contained in a phosphate buffered saline. In this case, the cell mass may be either a cell mass adhered to a cell culture substrate or a cell mass not adhered to a cell culture substrate. When a cell mass contained in a phosphate buffered saline is conventionally dispersed using a proteolytic enzyme, if a proteolytic enzyme is reacted with the cell mass for a long time, the proteolytic enzyme sometimes lyses the cell membrane of a cell which constitutes the cell mass. In contrast, since the fluororesin particle is used, the cell dispersion method of the present invention can sufficiently disperse a cell mass without damaging a cell which constitutes the cell mass in a phosphate buffered saline.

In addition, in the cell dispersion method of the present invention, a cell mass may contain a cervical cell. When a cell mass containing a mucus-attached cell such as a cervical cell is conventionally dispersed using a proteolytic enzyme, the proteolytic enzyme preferentially degrades the mucus. Consequently, the intended cell dispersion effect is insufficient. Furthermore, if a proteolytic enzyme is reacted with the cell mass for a long time, the proteolytic enzyme sometimes lyses the cell membrane of a cell which constitutes the cell mass. In contrast, since the fluororesin particle is used, the cell dispersion method of the present invention can sufficiently disperse a cell mass without damaging a cervical cell.

In the cell dispersion method of the present invention, the cell mass before mixed with a fluororesin particle may be fixed. Examples of a fixed cell mass include a cell mass collected from a uterine cervix and stored in an ethanol solution, and the like. When such a fixed cell mass is dispersed using a proteolytic enzyme, since the cell mass remains in a state of an aggregate under the reaction conditions similar to those for dispersion of a cell mass which is not fixed, dispersion of a cell mass is insufficient. On the other hand, if the proteolytic enzyme is reacted with a cell mass for a long time for dispersing a fixed cell mass, the proteolytic enzyme sometimes lyses the cell membrane of a cell which constitutes the cell mass. In contrast, since the fluororesin particle is used, the cell dispersion method of the present invention can sufficiently disperse a cell mass without damaging a cell which constitutes the fixed cell mass.

The cell dispersion method of the present invention may further contain a step of adding a visualizing agent for visualizing a cell, in other words, a step of contacting a cell mass with a visualizing agent for visualizing a cell (hereinafter referred to as a "visualizing step"). The visualizing step maybe carried out either concurrently with mixing of the cell mass and a fluororesin particle or after mixing of the cell mass and a fluororesin particle. In addition, in the present invention, a visualizing agent may be added to a cell mass or a fluororesin particle before carrying out mixing of the cell mass and a fluororesin particle.

In the present specification, a "visualizing agent" means an agent to make a cell which cannot be observed or is difficult to observe with a microscope observable or easy to observe, or an agent which makes a cell which cannot be detected by a flow cytometer detectable. The visualizing agent includes, for example, a staining agent which stains a cell membrane, a cytoplasm, a cell nucleus or an organelle of a cell, and the like. Specifically, the visualizing agent includes, for example, propidium iodide, which selectively stains a nucleus of a cell, trypan blue, which stains a whole cell, and the like. These visualizing agents do not stain a fluororesin particle. Therefore, even when a visualizing agent and a fluororesin particle are contained in a sample on which flow cytometry or cytological diagnosis is carried out, flow cytometry or cytological diagnosis can be carried out.

The cell dispersion method of the present invention can further contain an enhancing step in which the ratio of fluororesin particles entering into a gap among cells contained in a cell mass in the mixture of a cell mass and a fluororesin particle is increased. By carrying out such an enhancing step, the degree of lubrication of the interface between cells can be increased, to disperse a cell mass more efficiently. The enhancing step may be any step so long as the step increases the ratio of a fluororesin particle entering into a gap among cells contained in a cell mass to increase the shear stress between cells. Examples of the step include, for example, stir of the mixture of a cell mass and a fluororesin particle (referred to as a "stirring step"), applying an external force (for example, an injection power) to a fluororesin particle upon adding the fluororesin particle to a sample containing a cell mass, and the like. The stirring step includes stir by applying a rotational force to a mixture (such as, for example, stir with a pestle, a stir bar or the like), stir by vibration, and the like. When the enhancing step is a stirring step, the stirring time is not limited specifically, and the step can be carried out under those conditions wherein a cell dispersed by the cell dispersion method of the present invention is not damaged by an excess shear stress.

When a cell mass is conventionally dispersed using a great shear stress produced by stir with a mixer or the like, there is a possibility that a cell is damaged. In addition, when a shear stress is applied to an extent that a cell is not damaged, the cell dispersion effect is insufficient. In contrast, in the cell dispersion method of the present invention, a cell mass can be dispersed almost without using a shear stress. In addition, in the cell dispersion method of the present invention, even when a shear stress is applied to a certain extent by stir with a pestle, damage to a cell is decreased because of the lubricating action of a fluororesin particle. Consequently, by the cell dispersion method of the present invention, cells can be dispersed in a state that the shape of individual cells is kept. Therefore, the cell dispersed by the cell dispersion method of the present invention is suitable as a cell sample for flow cytometry or microscopic observation for measuring the shape of individual cells.

Here, in the present specification, "damage" includes, for example, breaking and cleavage of a cell, release of an intracellular substance out of a cell, and the like.

2. CELL DISPERSING AGENT

The cell dispersing agent of the present invention contains a fluororesin particle. The cell dispersing agent of the present invention can be used for the cell dispersion method. According to the cell dispersing agent of the present invention, since the agent contains a fluororesin particle, the interface between cells which constitute a cell mass is lubricated, whereby cells can be efficiently dispersed while inhibiting damage to a cell. The cell dispersing agent of the present invention may be either a fluororesin particle itself or a dispersion prepared by dispersing a fluororesin particle in a medium (for example, the liquid medium or the like).

The fluororesin which constitutes the fluororesin particle used in the cell dispersing agent of the present invention and the particle diameter of the fluororesin particle are similar to those described for the cell dispersion method of the present invention.

It is preferable that the cell dispersing agent of the present invention further contains a visualizing agent for visualizing a cell. A cell dispersed using such a cell dispersing agent of the present invention is suitable as a test sample for flow cytometry or microscopic observation, since the cell is visualized to be detectable or observable in flow cytometry or microscopic observation. The visualizing agent used in the cell dispersing agent of the present invention is similar to those described for the cell dispersion method of the present invention.

When the cell dispersing agent is an agent containing a fluororesin particle and a visualizing agent, the content of the visualizing agent in the cell dispersing agent can be appropriately depending on the number of cells to be dispersed, use of the cell dispersing agent, and the like.

3. CELL MEASUREMENT METHOD

The cell measurement method of the present invention contains a mixing step in which a cell mass composed of an aggregate of multiple cells is mixed with a fluororesin particle in a liquid medium, and a measurement step in which the mixture obtained in the mixing step is measured with a flow cytometer. The dispersed cell obtained in the mixing step is appropriate as a sample to be tested in cell measurement by flow cytometry, since damage to a cell is little and the cells are dispersed into individual cells.

The mixing step is carried out in similar manner as in the mixing of a cell mass and a fluororesin particle in the cell dispersion method. In addition, in the cell measurement method of the present invention, a step of adding a visualizing agent for visualizing a cell, in other words, a visualizing step in which a cell mass is contacted with a visualizing agent for visualizing a cell can be further contained prior to the measurement step. In addition, in the cell measurement method of the present invention, a stirring step in which the mixture obtained in the mixing step is stirred for a given period of time can be further contained prior to the measurement step. The visualizing step and the stirring step can be carried out by manipulation similar to the visualizing step and the stirring step in the cell dispersion method.

Dispersion of a cell mass using a fluororesin particle and measurement of a test sample containing the dispersed cell with a cell analyzer using flow cytometry will be hereinafter shown and explained.

FIG. 1 is the whole composition of a cell analyzer using a flow cytometry technique. An apparatus body 2 in cell analyzer 1 is equipped with an optical detector section 3 for detecting information on the size of a cell or a nucleus from a sample to be tested, a signal processing circuit (signal processor section) 4, a measurement controller section 6, a driving section 7 such as a motor, an actuator or a bulb, and various sensors 8. The measurement controller section 6 controls the behavior of the driving section 7 while processing signal from the sensor 8, thereby carrying out aspiration or measurement of the sample to be tested.

The cell analyzer 1 can be used in, for example, judging whether a cancer cell is contained in cervical cells or not.

Dispersion of a cell mass can be carried out as described below. A cell collected from a uterine cervix is fixed by adding the cell to a cell preservative liquid containing an alcohol solution (for example, a 55% by mass aqueous methanol solution), to give a cell suspension. In addition, a cell dispersing agent containing 60% by mass of a fluororesin particle and 1% by mass or less of propidium iodide (PI), which is a visualizing agent, is used as a cell dispersing agent. First, the cell dispersion agent is added to the cell suspension so that the concentration of a fluororesin particle is 0.003% by mass or more and 60% by mass or less, to prepare a mixture. Next, the obtained mixture is stirred to disperse a cell mass, to give a sample to be tested. Since PI is a visualizing agent which selectively stains the nucleus of a cell, fluorescence from the nucleus becomes detectable in a dispersed cell.

The obtained sample to be tested is recovered in a test tube and placed below a pipette of the apparatus body 2 (not illustrated), and aspirated by the pipette and fed to a flow cell.

Figure 2:
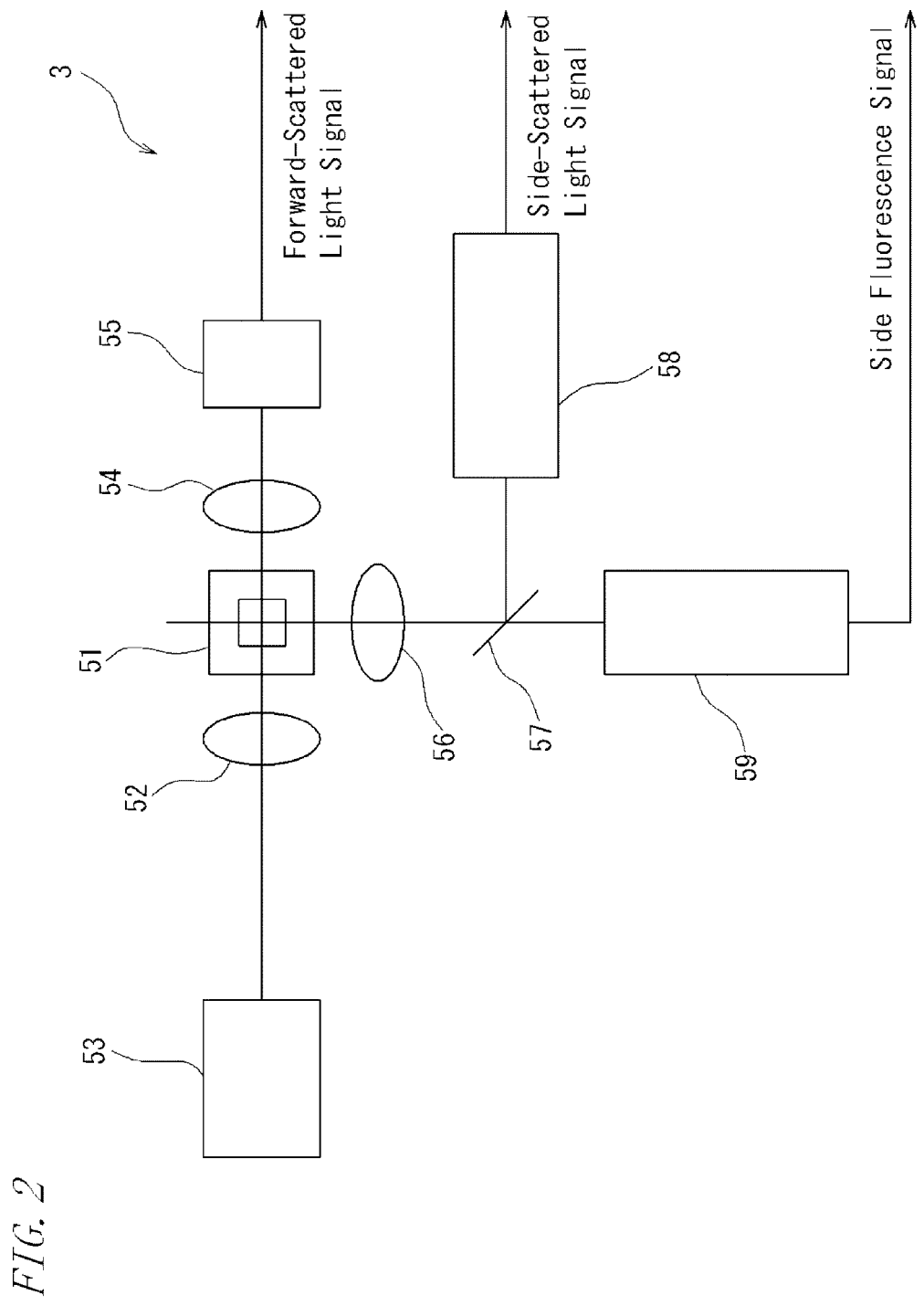
[FIG. 2] A figure showing the constitution of an optical detector section in the cell analyzer.

FIG. 2 shows the composition of the optical detector section 3. A lens system (optical system) 52 focuses laser light emitted from a semiconductor laser 53, which is a light source, to a sample to be tested flowing in a flow cell 51. The condenser lens 54 focuses forward-scattered light of a cervical cell and a fluororesin particle in the sample to be tested to a photodiode 55, which is a detector of scattered light. In addition, the condenser lens 56 focuses side-scattered light and side fluorescence of the cell or cell nucleus to a dichroic mirror 57. The dichroic mirror 57 reflects the side-scattered light to a photomultiplier 58, which is a detector of scattered light, and transmits the side fluorescence to a photomultiplier 59, which is a fluorescence detector. The photodiode 55, photomultipliers 58 and 59 convert the detected light into an electrical signal, and output a forward-scattered light signal, a side-scattered light signal and a side fluorescence signal, respectively. These outputs are amplified with a preamplifier which is not illustrated, and thereafter subjected to the signal processing circuit described above (see FIG. 1).

A value reflecting the size of a cell is obtained from the signal of detection of the forward-scattered light of a cervical cell. In addition, a value reflecting the size of the nucleus of a cell is obtained from the signal obtained from detection of the side fluorescence of a cervical cell. Here, the size of a cervical cell is about 60 μm and the size of a nucleus is 5 to 7 μm. When the cell becomes cancerous, the frequency of cell division abnormally increases, and the size of the nucleus becomes 10 to 15 μm. The N/C ratio (size of a nucleus/size of a cell) thus becomes larger relative to that of a normal cell. Therefore, by detection of the size of a cell and that of a nucleus, whether a cervical cell is a normal cell or a cancer cell can be judged.

On the other hand, a value reflecting the size of a fluororesin particle is obtained from the signal of detection of the forward-scattered light of a fluororesin particle. However, since the fluororesin particle is not stained with a PI visualizing agent, side fluorescence is substantially not generated. Consequently, the N/C ratio of a fluororesin particle is almost equal to zero, and the value becomes smaller than the N/C ratio of a normal cell and a cancer cell. Briefly, a fluororesin particle, a normal cell and a cancer cell can be distinguished on the basis of the N/C ratio. Therefore, even when a fluororesin particle is contained in a sample to be tested, it can be judged whether a cancer cell is contained in cervical cells or not. As described above, a cell dispersed using a fluororesin particle can be applied to flow cytometry.

EXAMPLES

While the present invention will be explained in detail on the basis of Examples, the present invention is not limited to these Examples at all.

Example 1

Cell Dispersion Effect by a Fluororesin Particle in a Specimen for Cytological Diagnosis of a Uterine Cervix Cells collected from a uterine cervix were fixed by a cell preservative liquid containing an alcohol [manufactured by Hologic Inc., trade name: PreservCyt™], to give a cell sample. The cell sample was subjected to centrifugation at 190×g for 5 minutes at room temperature, thereby recovering the cells. A portion of the recovered cells equivalent to 150 μL was collected with a pipette, to give a cell suspension.

On the other hand, 60 μL of 0.5% by mass trypan blue staining solution (manufactured by NACALAI TESQUE, INC.), which was a visualizing agent, and 87 μL of water were added to 3 μL of a water dispersion of a fluororesin particle [polytetrafluoroethylene particle (hereinafter referred to as a "PTFE particle"] [manufactured by ASAHI GLASS CO., LTD., trade name: Fluon™ PTFE Dispersion AD911L, average particle diameter of the PTFE particle (measured by a light scattering method): 0.25 μm, content of the PTFE particle: 60% by mass, liquid specific gravity: 1.52], to give a test sample. Here, trypan blue is a dye to visualize a whole cell (including a cell membrane and a cell nucleus).

Cell dispersion treatment was carried out by carrying out manipulation using the test sample as follows. First, the test sample was added to 150 μL of the cell suspension so that the concentration of a PTFE particle was 0.6% by mass and the concentration of trypan blue, which was a visualizing agent, was 0.1% by mass, to give a mixture. Thereafter, the resulting mixture was stirred at 4,000 rpm with a pestle, to give a sample of Example 1. Here, a cell suspension before cell dispersion treatment was used as a Reference Example.

Figure 3:
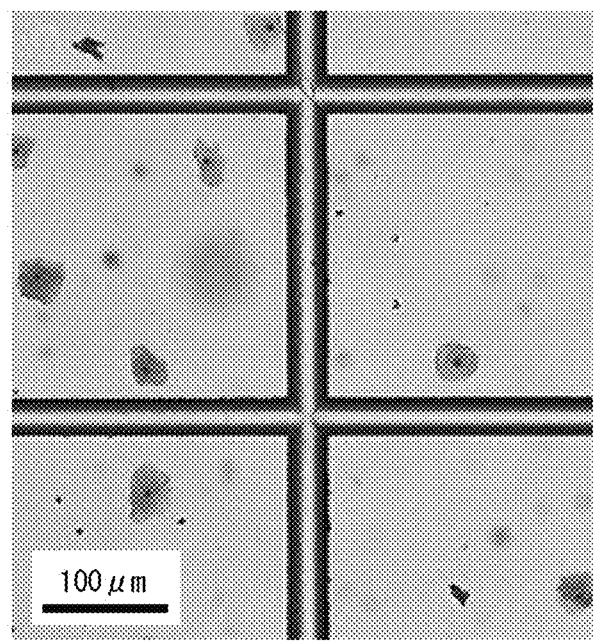
[FIG. 3] A micrograph of cells in a sample obtained by carrying out stir in the presence of a fluororesin particle in Example 1.

Each of the cell suspensions as the sample and a control of Example 1 was observed with a microscope. In Example 1, a micrograph of cells in the sample obtained by carrying out stir in the presence of a fluororesin particle is shown in FIG. 3. In addition, a micrograph of cells in a cell suspension is shown in FIG. 4 as a Reference Example.

Figure 4:
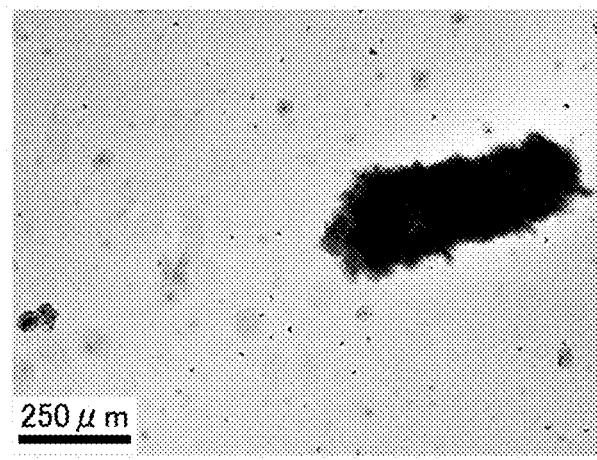
[FIG. 4] A micrograph of cells in a cell dispersion after stir in the absence of a fluororesin particle, as a reference example.

From the result shown in FIG. 4, it can be seen that cervical cells aggregate to form a cell mass in the cell suspension to which a fluororesin particle is not added. In contrast, from the result shown in FIG. 3, it can be seen that, when cell dispersion treatment is carried out using a fluororesin particle, the cervical cells in the sample are dispersed into individual cells in a state that the shape of a cell is kept.

From these results, it can be seen that the test sample containing a fluororesin particle exerts a cell dispersion effect and, moreover, can disperse a cell mass in a state that the shape of a cell is kept, thereby having an excellent property that damage to a cell is little. Therefore, the test sample containing a fluororesin particle is useful as a cell dispersing agent. In addition, it can be seen that the cell dispersion method using a fluororesin particle enables dissociation of cells in a cell suspension to disperse the cells into individual cells. In addition, from such a result, it can be seen that damage by the cell dispersion method of Example 1 is little.

Comparative Example 1

Cell Dispersion Method Using a Proteolytic Enzyme (Trypsin)

A trypsin-PBS solution was added to 150 μL of a cell suspension similar to that used in Example 1 so that the final concentration of trypsin was 0.01% by mass, and the mixture was incubated at 37° C. for a given period of time (1.5, 3, or 46 hours). Each cell after incubation was then observed with a microscope. The result of observation of cells after carrying out incubation in Comparative Example 1 is shown in FIG. 5, the result of observation of cells after carrying out incubation for 3 hours in Comparative Example 1 being shown in FIG. 6, and the result of observation of cells after carrying out incubation for 46 hours in Comparative Example 1 being shown in FIG. 7.

Figure 5:
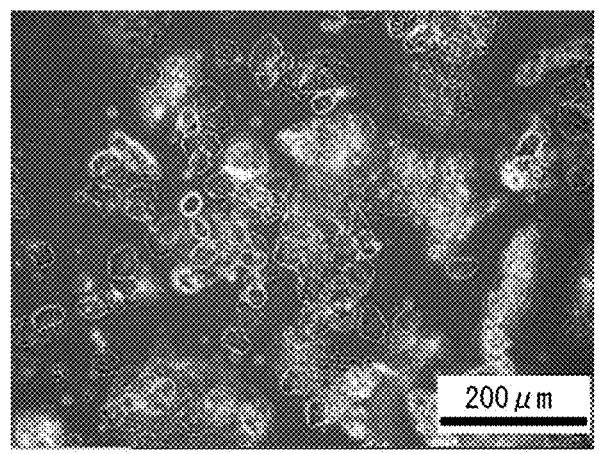
[FIG. 5] A micrograph of cells after carrying out incubation with trypsin for 1.5 hours in Comparative Example 1.
Figure 6:
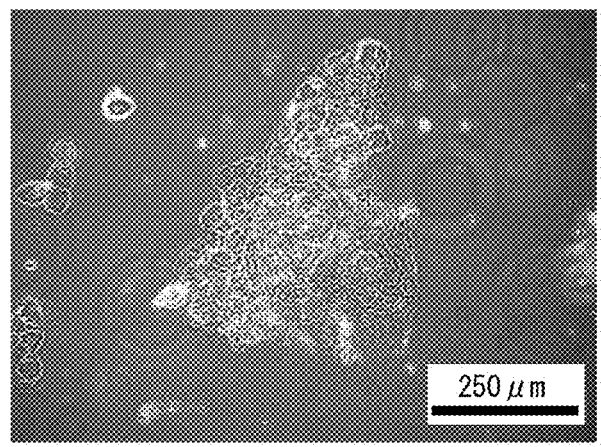
[FIG. 6] A micrograph of cells after carrying out incubation with trypsin for 3 hours in Comparative Example 1.
Figure 7:
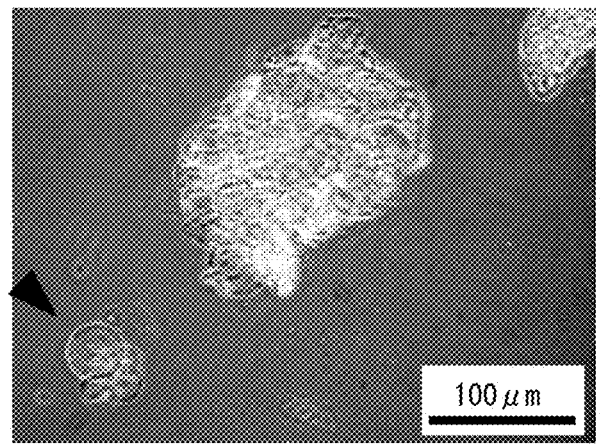
[FIG. 7] A micrograph of cells after carrying out incubation with trypsin for 46 hours in Comparative Example 1.

From the result shown in each of FIGS. 5, 6 and 7, it can be seen that, when carrying out incubation with trypsin, the number of individual cells dissociated from a cell mass and dispersed is smaller as compared to that in Comparative Example 1. In addition, as shown by Cell 1 in FIG. 7, an abnormal cell which swelled to be in a blister state was observed. It can be considered that such results are caused by damage to a cell membrane and disturbance in the balance of osmotic pressure due to incubation of a cell with trypsin for a long time.

These results show that the cell dispersion method of Comparative Example 1 using trypsin is insufficient to dissociate a cell mass in a cell suspension containing a cervical cell fixed by a cell preservative liquid containing an alcohol to disperse the cell mass into individual cells. In addition, it can be seen that the cell dispersion method of Comparative Example 1 damages a cell.

Comparative Example 2

Cell Dispersion Method Using a Physical Force

Figure 8:
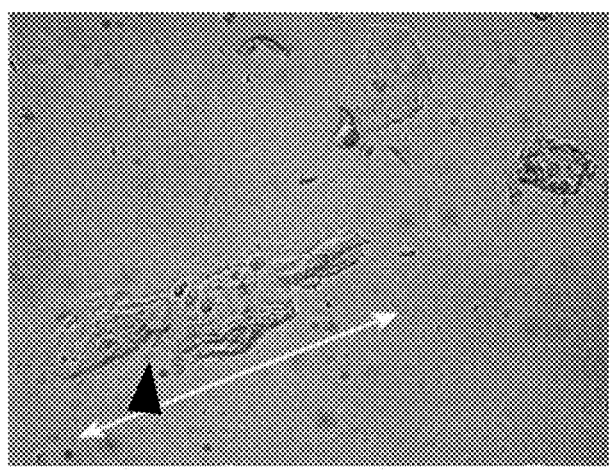
[FIG. 8] A micrograph of cells in a cell dispersion after stir with a pestle in Comparative Example 2.
Figure 9:
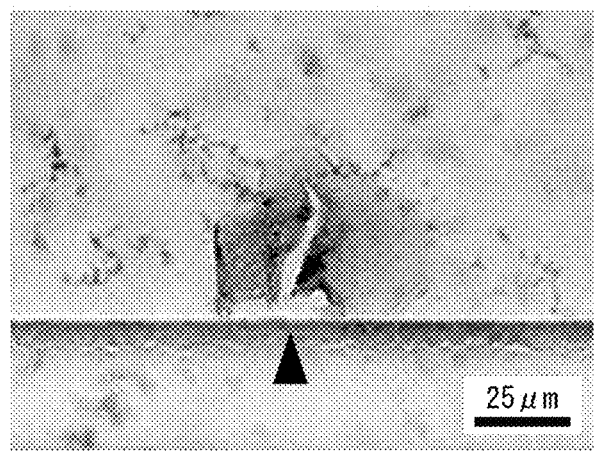
[FIG. 9] A micrograph of cells in a cell dispersion after stir with a pestle in Comparative Example 2.

One-hundred and fifty microliters of a cell suspension similar to that used in Example 1 was collected in a plastic tube. Thereafter, the cell suspension was stirred at 4,000 rpm with a pestle for 3 minutes. Next, the stirred cell was observed with a microscope. In addition, propidium iodide solution was added to 150 μL of the stirred cell suspension to have a final concentration of 10 μg/mL to stain a nucleus, and the cell nucleus of a cell in the cell suspension obtained after staining was observed with a microscope. In Comparative Example 2, micrographs of cells in the cell suspension after stir with a pestle are shown in FIGS. 8 and 9. In addition, in Comparative Example 2, a micrograph of a stained image of cell nuclei of cells in the cell suspension after stir with a pestle is shown in FIG. 10.

Figure 10:
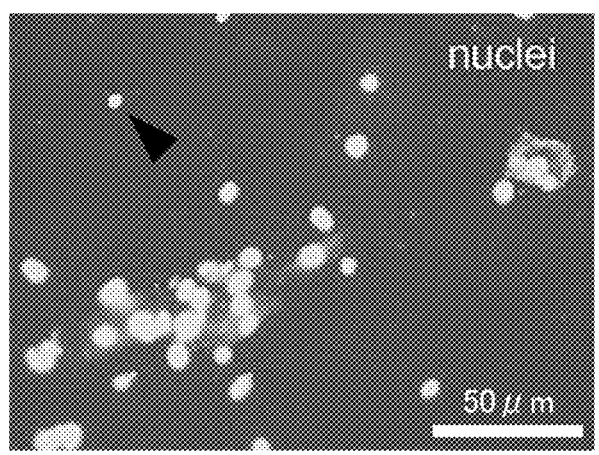
[FIG. 10] A micrograph of a stained image of cell nuclei of cells in a cell dispersion after stir with a pestle in Comparative Example 2.

From the results shown in each of FIGS. 8 to 10, it can be seen that a method for dispersing a cell mass using only a physical force by stir with a pestle in the absence of a fluororesin particle merely stretches a cell mass (see an arrowhead in FIG. 8), breaks a dispersed cell (see an arrowhead in FIG. 9), and, moreover, remove a cell nuclei out of the membrane of a cell (enucleation) (see an arrowhead in FIG. 10).

From these results, it can be seen that the cell dispersion method of Comparative Example 2 using only a physical force damages a cell. There is a possibility that such damage to a cell negatively affects cytological diagnosis and measurement by flow cytometry. In contrast, the cell dispersion method of Example 1 wherein stir was carried out in the presence of a fluororesin particle can reduce damage to a cell by a physical force, by a lubricating action of the fluororesin particle.

As described above, in the cell dispersion method of Comparative Example 1 using a proteolytic enzyme and the cell dispersion method of Comparative Example 2 using only a physical force, the cell dispersion effect is insufficient or the shape of a cell cannot be kept. In contrast, in the cell dispersion method of Example 1, cells are sufficiently dispersed and damage to a cell is little. Therefore, from these results, it is suggested that a cell dispersing agent containing a fluororesin particle (PTFE particle) or a cell dispersion method using the agent enables preparation of a sample to be tested suitable for cytological diagnosis or measurement by flow cytometry. In addition, it can be seen that a cell dispersion method using a cell dispersing agent containing a fluororesin particle is suitable as a pretreatment in cytological diagnosis to observe individual cells or in flow cytometry to measure individual cells.

Example 2

Examination of the Concentration of a Fluororesin Particle

A portion of the cells equivalent to approximately 10 μL was collected from the cell suspension similar to that used in Example 1, and 60 μL of a water dispersion of a fluororesin particle similar to that used in Example 1 was added thereto, to prepare a mixture. Here, the concentration of a fluororesin particle (PTFE particle) in such a mixture is 54% by mass. The resulting mixture was stirred at 4,000 rpm with a pestle for 3 minutes. The stirred mixture was used as a sample of Example 2.

Next, the sample of Example 2 was observed with a microscope. In Example 2, a micrograph of cells in the sample obtained by carrying out stir in the presence of a fluororesin particle is shown in FIG. 11.

Figure 11:
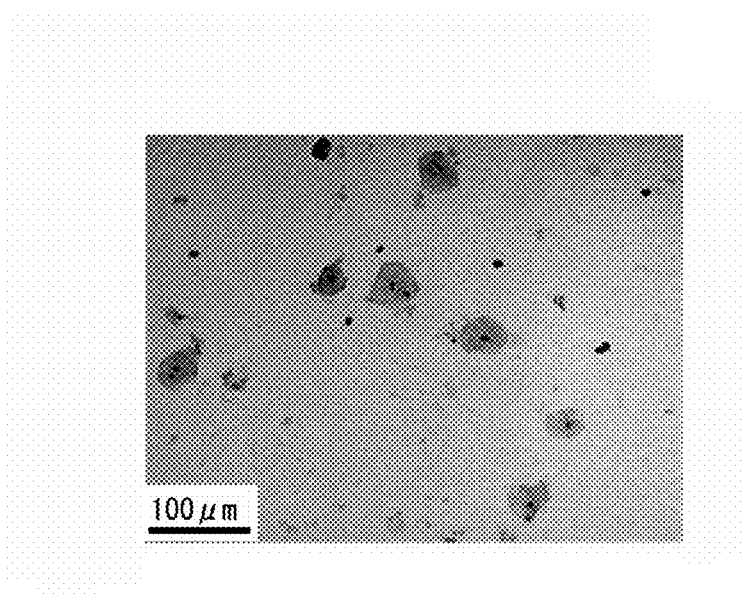
[FIG. 11] A micrograph of cells in a sample obtained by carrying out stir in the presence of a fluororesin particle in Example 2.

From the result shown in FIG. 11, it can be seen that, even when the cell dispersing agent is used and the concentration of PTFE particle is set to be the above-mentioned concentration, a cell mass can be dissociated to disperse into individual cells in a state that the shape of a cell is kept and damage to a cell is little.

Example 3

Cell Dispersion Effect on Fixed Culture Cells

Culture cells were suspended into a medium and cultured in Teflon™ dish, whereby a spherical assembly of cells referred to as a spheroid was formed in the medium. The medium containing the spheroid was subjected to centrifugation at 190×g for 5 minutes at room temperature, to recover a cell group containing the spheroid. A cell preservative liquid similar to that used in Example 1 described above was added to the resulting cell group to immobilize the cells, to give a cell suspension. Thereafter, trypan blue was added to 150 μL of the cell suspension containing the fixed culture cell to have a final concentration of 0.1% by mass, to stain the cell. A cell dispersing agent similar to that in Example 1 described above was added to the stained cell suspension so that the final concentration of a PTFE particle was 0.6% by mass, to give a mixture. Thereafter, the resulting mixture was stirred at 4,000 rpm with a pestle for 3 minutes. The stirred mixture was used as a sample of Example 3.

Next, the sample of Example 3 was observed with a microscope. In Example 3, a micrograph of cells in the sample obtained by stir in the presence of a cell dispersing agent is shown in FIG. 12.

Figure 12:
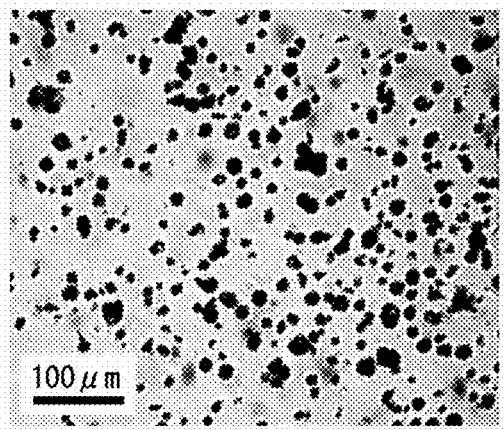
[FIG. 12] A micrograph of cells in a sample obtained by carrying out stir in the presence of a fluororesin particle in Example 3.

From the result shown in FIG. 12, it can be seen that, even when cells are fixed, a cell mass is dissociated to disperse into individual cells in a state that the shape of a cell is kept and damage to a cell is little.

Cell dispersion effect and damage to a cell in each of the cell dispersion methods of Examples 1 to 3, Comparative Examples 1 and 2 described above are summarized in Table 1.

TABLE 1

|  | Cell Dispersion Effect | Damage to Cell |
| --- | --- | --- |
| Example 1 | great | little |
| Example 2 | great | little |
| Example 3 | great | little |
| Comparative Example 1 | small | severe |
| Comparative Example 2 | small | severe |

As shown in Table 1, in the cell dispersion method of Comparative Example 1 using a proteolytic enzyme and in the cell dispersion method of Comparative Example 2 using only a physical force, it can be seen that dispersion of a cell mass is insufficient and, moreover, damage to a cell is severe.

As compared to these results, it can be seen that, a cell mass is dissociated to disperse into individual cells, and, moreover, damage to a cell is little, in each of the cell dispersion methods of Examples 1, 2 and 3 (the cell dispersion method of the present invention).

Test Example 1

Examination of Influence of the Concentration of a Fluororesin Particle on Cell Dispersion Effect Using a water dispersion of a fluororesin particle and a cell suspension similar to those used in Example 1, influence of the concentration of a fluororesin particle in cell dispersion effect was examined as follows.

A water dispersion of a fluororesin particle was added to a cell suspension so that the final concentration of a PTFE particle, which is a fluororesin particle, was 0.003% by mass, and trypan blue was also added thereto, so that the final concentration was 0.1% by mass, to give a mixture. The resulting mixture was stirred at 4,000 rpm using a stir bar for 3 minutes (Example 4). The stirred mixture was used as a sample of Example 4.

In addition, manipulation similar to that in Example 4 was carried out except that the concentration of a PTFE particles was set to be 0.03% by mass (Example 5), 0.06% by mass (Example 6), 0.3% by mass (Example 7), 3% by mass (Example 8) or 60% by mass (Example 9), to give samples of Examples 5 to 9.

Figure 13:
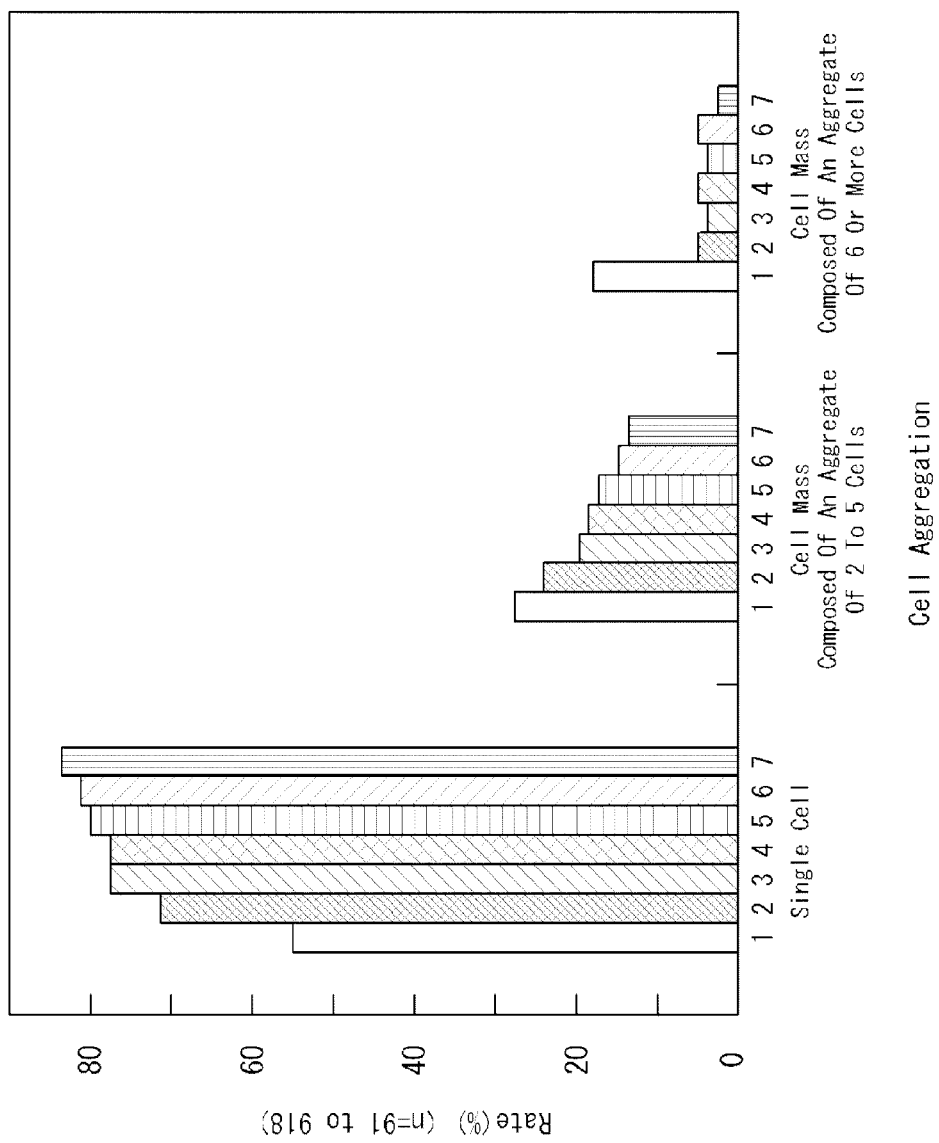
[FIG. 13] A graph showing the relationship between the concentration of a PTFE particle and the ratio of single cells and cell masses, respectively.

Cells in each sample were observed with a microscope, and ratio of each of a "single cell", a "cell mass composed of an aggregate of 2 to 5 cells", and a "cell mass composed of an aggregate of 6 or more cells" in each sample was examined. Here, for comparison, ratio of a single cell and a cell mass in a cell suspension to which a PTFE particle is not added was examined (Comparative Example 3). A graph showing the relationship between the concentration of a PTFE particle and a single cell and a cell mass, respectively, is shown in FIG. 13. In FIG. 13, Lane 1 indicates Comparative Example 1, Lane 2 being Example 4, Lane 3 being Example 5, Lane 4 being Example 6, Lane 5 being Example 7, Lane 6 being Example 8 and Lane 7 being Example 9.

From the result shown in FIG. 13, it can be seen that even when the concentration of a PTFE particle is any of 0.003% by mass, 0.03% by mass, 0.06% by mass, 0.3% by mass, 3% by mass or 60% by mass as in Examples 4 to 9, the ratio of a "cell mass composed of an aggregate of 2 to 5 cells" or a "cell mass composed of an aggregate of 6 or more cells" in a sample decreases and the ratio of a "single cell" increases to over 70% as compared to those in a cell suspension to which a PTFE particle is not added. Therefore, it is suggested that the cell dispersion methods of Examples 4 to 9 using a fluororesin particle exerts a cell dispersion effect even when the concentration of a fluororesin particles ranges from as low as 0.003% by mass to as high as 60% by mass.

Test Example 2

Examination of Influence of Presence of a Fluororesin Particle on Cell Dispersion Effect Using a cell derived from a uterine cervix, influence of presence of a fluororesin particle on cell dispersion effect was examined.

A water dispersion of a fluororesin particle was added to a cell suspension similar to that used in Example 1, so that the final concentration of a PTFE particle was 0.003% by mass, and trypan blue was also added thereto so that the final concentration was 5% by mass. The resulting mixture was stirred at 4,000 rpm for 3 minutes (Example 10). The stirred mixture was used as a sample of Example 10. In addition, manipulation similar to that in Example 10 was carried out except that stirring time was changed to 9 minutes, to give a sample of Example 11.

Figure 14:
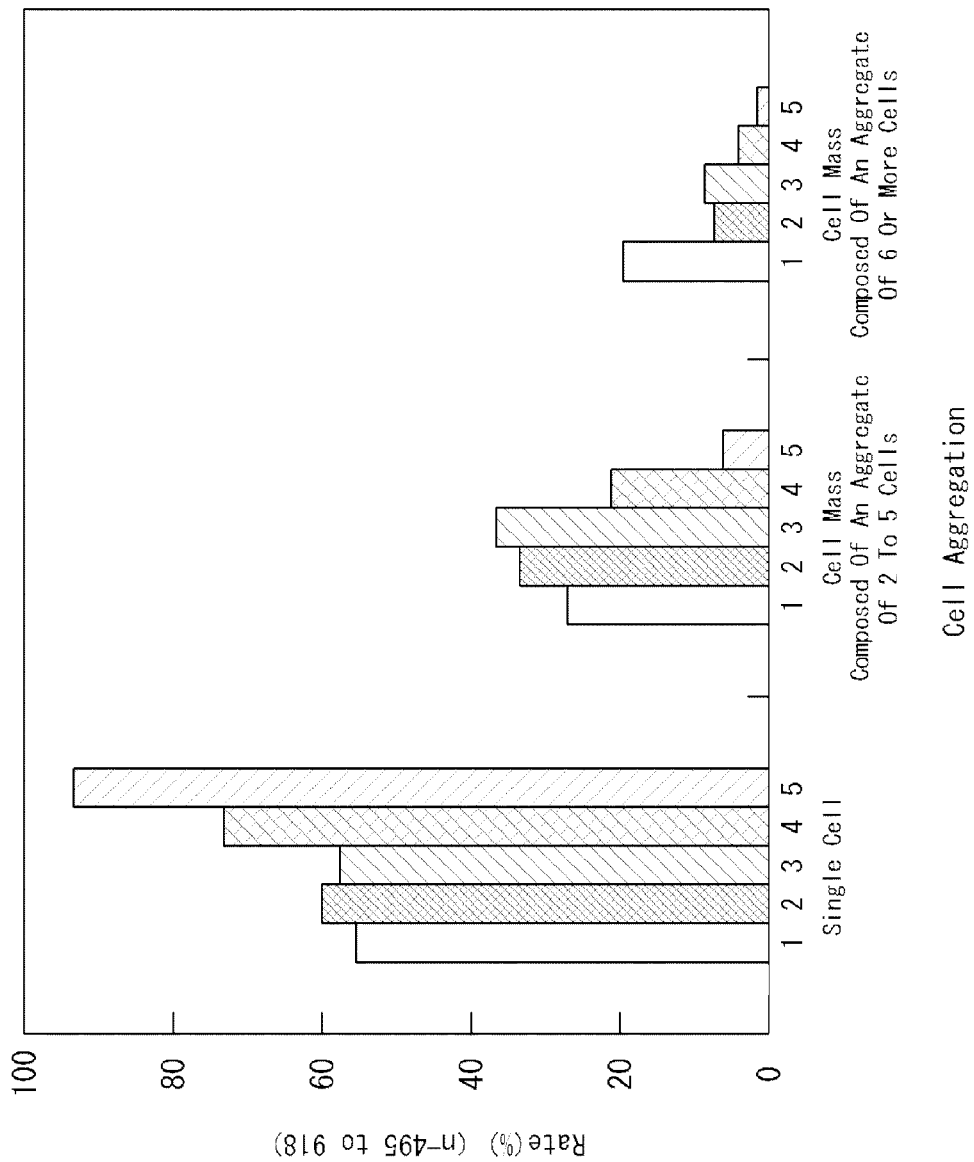
[FIG. 14] A graph showing the relationship between presence of a PTFE particle and the ratio of single cells and cell masses, respectively.

Cells in each sample were observed with a microscope, and the ratio of a "single cell", a "cell mass composed of an aggregate of 2 to 5 cells" and a "cell mass composed of an aggregate of 6 or more cells" in a cell suspension was examined. Here, for comparison, the ratio of a single cell and a cell mass was examined as in the same manner as described above, for the cell suspension to which a PTFE particle was not added (Comparative Example 4), and samples of Comparative Examples 5 and 6 obtained by stirring a cell suspension for 3 minutes (Comparative Example 5) or 9 minutes (Comparative Example 5) without adding a cell dispersion agent. A graph of the relationship between presence of a PTFE particle and the ratio of each of a single cell and a cell mass is shown in FIG. 14. In FIG. 14, Lane 1 indicates Comparative Example 4, Lane 2 being Comparative Example 5, Lane 3 being Comparative Example 6, Lane 4 being Example 10 and Lane 5 being Example 11.

From the result shown in FIG. 14, when a cell suspension is stirred without adding a PTFE particle (Comparative Examples 5 and 6), the ratio of a "single cell" did not increase regardless of the length of the stirring time, and the ratio was about the same as that of a "single cell" in a cell suspension to which a PTFE particle was not added (Comparative Example 4). On the other hand, when stir was carried out in the presence of a PTFE particle (Examples 10 and 11), it can be seen that the ratio of a "cell mass composed of an aggregate of 2 to 5 cells" and a "cell mass composed of an aggregate of 6 or more cells" decreases as compared to the ratio of a "single cell" in a cell suspension which is not subjected to a cell dispersion treatment, and that the ratio of a "single cell" increases to over 70%.

Consequently, it can be seen that, when stir is carried out in the presence of a PTFE particle, an excellent cell dispersion effect is exerted as compared to that in the case that stir is carried out without using a PTFE particle. In addition, while the ratio of a "single cell" in Example 10 is 70%, the ratio of a "single cell" in Example 11 is 94%. From these results, it can be seen that the longer the stirring time is, the more the ratio of a "cell mass composed of an aggregate of 2 to 5 cells" and a "cell mass composed of an aggregate of 6 or more cells" remarkably decreases and the more the ratio of a "single cell" increases under the conditions wherein stir is carried out in the presence of a PTFE particle. Therefore, it is suggested that, even when the concentration of a PTFE particle is low, a high dispersion effect can be obtained by setting the stirring time to be optimum amount of time.

The invention claimed is:

1. A cell dispersion method, comprising a step of separating a cell mass composed of an aggregate of multiple cells into individual cells to disperse the cells in a liquid medium, wherein the cell mass is mixed with a fluororesin particle in a liquid medium.

2. The cell dispersion method according to claim 1, wherein said fluororesin particle is a particle consisting of at least one member selected from the group consisting of polytetrafluoroethylene (PTFE), tetrafluoroethylene-perfluoroalkyl vinyl ether copolymer (PFA), tetrafluoroethylene-hexafluoropropylene copolymer (FEP), ethylenetetrafluoroethylene copolymer (ETFE), polyvinylidene fluoride (PVDF), polychlorotrifluoroethylene (PCTFE) and ethylene-chlorotrifluoroethylene copolymer (ECTFE).

3. The cell dispersion method according to claim 1, wherein the cell mass before being mixed with a fluororesin particle is attached to a cell culture substrate.

4. The cell dispersion method according to claim 1, wherein the cell mass before being mixed with a fluororesin particle is contained in a medium.

5. The cell dispersion method according to claim 1, wherein the cell mass before being mixed with a fluororesin particle is contained in a phosphate buffered saline.

6. The cell dispersion method according to claim 1, wherein said cell mass contains a mucus aggregated cell.

7. The cell dispersion method according to claim 1, wherein said cell mass contains a cervical cell.

8. The cell dispersion method according to claim 1, wherein the cell mass before being mixed with a fluororesin particle is fixed.

9. The cell dispersion method according to claim 1 further comprising a contacting step in which a cell mass is contacted with a staining agent for staining a cell.

10. The cell dispersion method according to claim 1 further comprising an enhancing step in which the ratio of a fluororesin particle entering into a gap among cells contained in a cell mass in said mixture of a cell mass and a fluororesin particle is increased.

11. The cell dispersion method according to claim 10, wherein said enhancing step is a stirring step in which said mixture is stirred.

12. The cell dispersion method according to claim 1, wherein the concentration of a fluororesin particle in said mixture is 0.003% by mass or more and 60% by mass or less.

13. The cell dispersion method according to claim 1, wherein said fluororesin particle has a diameter from 0.01 to 200 μm.

* * * * *